US008471074B2

(12) United States Patent
Krafft et al.

(10) Patent No.: US 8,471,074 B2
(45) Date of Patent: Jun. 25, 2013

(54) PROCESS FOR THE MANUFACTURE OF DICHLOROPROPANOL

(75) Inventors: Philippe Krafft, Rhode Saint Genese (BE); Patrick Gilbeau, Braine-le-Comte (BE); Dominique Balthasart, Brussels (BE); Maurizio Paganin, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 839 days.

(21) Appl. No.: 12/529,778

(22) PCT Filed: Mar. 13, 2008

(86) PCT No.: PCT/EP2008/052972
§ 371 (c)(1),
(2), (4) Date: Sep. 3, 2009

(87) PCT Pub. No.: WO2008/110588
PCT Pub. Date: Sep. 18, 2008

(65) Prior Publication Data
US 2010/0105964 A1    Apr. 29, 2010

Related U.S. Application Data
(60) Provisional application No. 61/013,707, filed on Dec. 14, 2007.

(30) Foreign Application Priority Data

Mar. 14, 2007    (FR) ..................................... 07 53837

(51) Int. Cl.
    *C07C 31/36*    (2006.01)
(52) U.S. Cl.
    USPC ......................................................... 568/841
(58) Field of Classification Search
    USPC ......................................................... 568/841
    See application file for complete search history.

(56) References Cited

U.S. PATENT DOCUMENTS

| | | |
|---|---|---|
| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,860,146 A | 11/1955 | Furman et al. |
| 2,726,072 A | 12/1955 | Herman |
| 2,733,195 A | 1/1956 | Miller |
| 2,611,227 A | 10/1957 | O'Connor |
| 2,829,124 A | 4/1958 | Napravnik et al. |
| 2,675,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,581 A | 11/1964 | Vandenberg |
| 3,158,680 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |

(Continued)

FOREIGN PATENT DOCUMENTS

| | | |
|---|---|---|
| BE | 422877 A | 8/1937 |
| CN | 1135533 | 11/1996 |

(Continued)

OTHER PUBLICATIONS

Wu, Guoying, et al., "Preparation of Biodiesel and Glycerol by Methyl Esterification of Cottonseed Oil," China Oil and Fat, (2003), vol. 28, Iss. 4, 70-73, pp. 1-9.
Zhu Shiyong, "Production and Prospects of the World's Natural Glycerin," Cereals and Oils, (1997), Issue 01, 33-38, pp. 1-15.
Arthur J. Hill et al, "A Synthesis of Beta-Chloro-Ally Chloride," Journal American Chemical Society, 1922, 44(11), 2582-2595.
Physical and Chemical Dictionary (5th Edition), Feb. 20, 1998 (with attached English translation of cited excerpt).
Encyclopaedia CHIMICA, No. 8, $1^{st}$ Edition, Feb. 28, 1962 1-1, (with attached English translation of cited excerpt).
Encyclopaedia CHIMICA, No. 2, $1^{st}$ Edition, Jun. 30, 1960, 1-2, (with attached English translation of cited excerpt).
Klaus Gottlieb, et al., "Glycerine—A Sustainable Raw Material," Chem. Ing. Tech. 66 (1994) Nr.1, S, 64-66 (with attached English translation).
Wissenschaft & Technik, Mar. 1995, pp. 139-142 (no translation).
Milchert et al., "Dehydrochlorination of Glycerol Dichlorohydrin to Epichlorohydrin," *Chem. Papers*, 49 (3) 133-136 (1995).
M. Demarquay, "De La Glycerine," Librairie de la Faculté de Médecine, Paris 1863 (no translation).
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.

(Continued)

*Primary Examiner* — Joseph K. McKane
*Assistant Examiner* — Samantha Shterengarts
(74) *Attorney, Agent, or Firm* — Oblon, Spivak, McClelland, Maier & Neustadt, L.L.P.

(57) ABSTRACT

Process for manufacturing dichloropropanol according to which, a) in a liquid reaction medium containing water, which is in contact with a gaseous phase, glycerol is reacted with hydrogen chloride under a partial pressure of hydrogen chloride in the gaseous phase greater than 0.2 bar absolute, and b) at least part of the liquid reaction medium and optionally part of the gaseous phase from step a) is (are) subjected to at least one separation operation and, prior to said separation operation, the part of the liquid reaction medium and the part of the gaseous phase from step a) is (are) subjected to bi) at least one treatment for reducing the weight ratio between the hydrogen chloride and the water in the part of the liquid reaction medium so as to attain a ratio less than or equal to the weight ratio between the hydrogen chloride and the water in the binary azeotropic hydrogen chloride/water composition at total pressure of the separation operation, and/or bii) at least one treatment for reducing the weight ratio between the water and the dichloropropanol in the part of the liquid reaction medium so as to attain a ratio less than or equal to the weight ratio between the water and the dichloropropanol in the ternary water/dichloropropanol/hydrogen chloride azeotrope at total pressure of the separation operation.

12 Claims, 5 Drawing Sheets

U.S. PATENT DOCUMENTS

Figure 1:
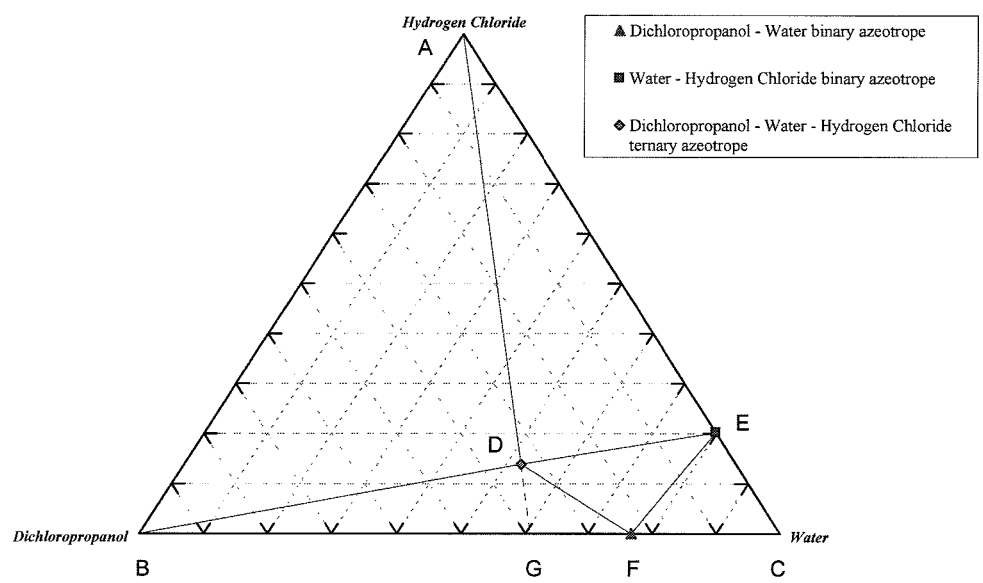

| | | | |
|---|---|---|---|
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,104,434 A | 8/1978 | Johnson |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,309,394 A | 1/1982 | Hudson |
| 4,322,367 A | 3/1982 | Silvis |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,898,644 A | 2/1990 | Van Horn |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,766,270 A | 6/1998 | Neuman et al. |
| 5,779,915 A | 7/1998 | Becker et al. |
| 5,908,946 A | 6/1999 | Stern et al. |
| 5,955,043 A | 9/1999 | Neuman et al. |
| 5,993,974 A | 11/1999 | Fukushima et al. |
| 6,024,839 A | 2/2000 | Schufeldt |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,428,759 B1 | 8/2002 | Smith et al. |
| 6,521,794 B2 | 2/2003 | Hirota |
| 6,589,497 B2 | 7/2003 | Smith |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 6,831,201 B2 | 12/2004 | Katsuura et al. |
| 7,126,032 B1 | 10/2006 | Aiken |
| 7,128,890 B2 | 10/2006 | Ollivier |
| 7,453,008 B2 | 11/2008 | Ko et al. |
| 7,557,253 B2 | 7/2009 | Gilbeau |
| 7,584,629 B2 | 9/2009 | Sohn et al. |
| 7,615,670 B2 | 11/2009 | Gilbeau |
| 8,106,246 B2 | 1/2012 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0251831 A1 | 11/2007 | Kaczur et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0105964 A1 | 4/2010 | Krafft et al. |
| 2011/0028683 A1 | 2/2011 | Gilbeau et al. |
| 2012/0010420 A1 | 1/2012 | Gilbeau et al. |
| 2012/0199493 A1 | 8/2012 | Krafft et al. |
| 2012/0199786 A1 | 8/2012 | Gilbeau |

FOREIGN PATENT DOCUMENTS

| | | |
|---|---|---|
| CN | 1296003 A | 5/2001 |
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 4335311 A1 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |

| | | | | | | |
|---|---|---|---|---|---|---|
| EP | 0563720 A1 | 10/1993 | | JP | 61 112066 A | 5/1986 |
| EP | 0568389 A1 | 11/1993 | | JP | 61-140532 | 6/1986 |
| EP | 0582201 A2 | 2/1994 | | JP | 61236749 A | 10/1986 |
| EP | 0 618 170 | 10/1994 | | JP | 62242638 A | 10/1987 |
| EP | 0 916 624 | 5/1999 | | JP | 63195288 A | 8/1988 |
| EP | 0919551 A1 | 6/1999 | | JP | 2-137704 | 5/1990 |
| EP | 0 774 450 | 2/2000 | | JP | 03014527 A | 1/1991 |
| EP | 0 979 671 | 2/2000 | | JP | 3223267 A | 10/1991 |
| EP | 1059278 A2 | 12/2000 | | JP | 03223267 A | 10/1991 |
| EP | 1106237 A1 | 6/2001 | | JP | 04089440 A | 3/1992 |
| EP | 1153887 A2 | 11/2001 | | JP | 04-217637 | 8/1992 |
| EP | 1163946 A1 | 12/2001 | | JP | 06-009589 | 1/1994 |
| EP | 1231189 A1 | 8/2002 | | JP | 625196 B2 | 4/1994 |
| EP | 1298154 A1 | 4/2003 | | JP | 06184024 A | 7/1994 |
| EP | 1411027 A1 | 4/2004 | | JP | 6321852 A | 11/1994 |
| EP | 1752435 A1 | 2/2007 | | JP | 08-003087 | 1/1996 |
| EP | 1752436 A1 | 2/2007 | | JP | 859593 | 3/1996 |
| EP | 1760060 A1 | 3/2007 | | JP | 09-299953 | 11/1997 |
| EP | 1762556 A1 | 3/2007 | | JP | 10139700 A | 5/1998 |
| EP | 1770081 A1 | 4/2007 | | JP | 10218810 A | 8/1998 |
| EP | 1772446 A1 | 4/2007 | | JP | 1998218810 A | 8/1998 |
| EP | 1775278 A1 | 4/2007 | | JP | 20020265986 A | 12/2000 |
| EP | 2 085 364 | 8/2009 | | JP | 2001-037469 | 2/2001 |
| FR | 1 306 231 | 10/1961 | | JP | 2001-213827 A | 8/2001 |
| FR | 1 147 388 | 10/1964 | | JP | 2001-261308 | 9/2001 |
| FR | 1476073 A | 4/1967 | | JP | 2001-1261581 A | 9/2001 |
| FR | 1 577 792 | 8/1968 | | JP | 2001-276572 | 10/2001 |
| FR | 2151107 | 4/1973 | | JP | 2002-02033 A2 | 1/2002 |
| FR | 2180138 | 5/1973 | | JP | 20020038195 A | 2/2002 |
| FR | 2 217 372 | 2/1974 | | JP | 20000344692 A | 8/2002 |
| FR | 2565229 A1 | 12/1985 | | JP | 2002-363153 A | 12/2002 |
| FR | 2752242 A1 | 2/1998 | | JP | 2003-89680 A | 3/2003 |
| FR | 2862644 A1 | 5/2005 | | JP | 2003081891 A | 3/2003 |
| FR | 2868419 A1 | 10/2005 | | JP | 2003-183191 | 7/2003 |
| FR | 2869612 A1 | 11/2005 | | JP | 2003-206473 | 7/2003 |
| FR | 2869613 A1 | 11/2005 | | JP | 2004-518102 | 6/2004 |
| FR | 2872504 A1 | 1/2006 | | JP | 2004-216246 | 8/2004 |
| FR | 2881732 A1 | 8/2006 | | JP | 2005007841 A2 | 1/2005 |
| FR | 2885903 A1 | 11/2006 | | JP | 2005097177 A2 | 4/2005 |
| FR | 2 912 743 | 8/2008 | | JP | 2005-513064 | 5/2005 |
| FR | 2 913 683 | 9/2008 | | JP | 2005-154292 | 6/2005 |
| FR | 2913683 A1 | 9/2008 | | JP | 2007-008898 | 1/2007 |
| FR | 2 917 411 | 12/2008 | | JP | 2009-263338 | 11/2009 |
| FR | 2918058 A1 | 1/2009 | | KR | 900006513 | 11/1987 |
| FR | 2925045 A1 | 6/2009 | | KR | 1019920003099 B1 | 4/1992 |
| FR | 2929611 A1 | 10/2009 | | KR | 10-514819 B1 | 9/2005 |
| FR | 2935699 A1 | 3/2010 | | PL | 136598 | 3/1986 |
| FR | 2935968 A1 | 3/2010 | | PL | 162910 | 1/1994 |
| GB | 14767 A | 1/1914 | | SU | 123153 | 1/1959 |
| GB | 406345 | 8/1932 | | SU | 1125226 | 11/1984 |
| GB | 404938 A | 1/1934 | | SU | 1159716 | 6/1985 |
| GB | 467481 A | 6/1937 | | SU | 1685969 | 10/1991 |
| GB | 541357 A | 11/1941 | | WO | WO 95/14635 | 6/1995 |
| GB | 724222 | 6/1952 | | WO | WO 95/14639 | 6/1995 |
| GB | 679536 A | 9/1952 | | WO | WO 96/07617 | 3/1996 |
| GB | 702143 A | 1/1954 | | WO | WO 96/15980 | 5/1996 |
| GB | 758665 | 10/1954 | | WO | WO 97/48667 | 12/1997 |
| GB | 736641 A | 9/1955 | | WO | WO 98/37024 | 8/1998 |
| GB | 799567 A | 8/1958 | | WO | WO 99/14208 | 3/1999 |
| GB | 984446 A | 2/1965 | | WO | WO 9932397 A1 | 7/1999 |
| GB | 984633 A | 3/1965 | | WO | WO 0024674 A1 | 5/2000 |
| GB | 1046521 A | 10/1966 | | WO | WO 01/43762 | 6/2001 |
| GB | 1083594 A | 9/1967 | | WO | WO 0141919 A1 | 6/2001 |
| GB | 1286893 A | 8/1972 | | WO | WO 0186220 A2 | 11/2001 |
| GB | 1387668 A | 3/1975 | | WO | WO 02/26672 A2 | 4/2002 |
| GB | 1 493 538 | 4/1975 | | WO | WO 02/059536 | 8/2002 |
| GB | 1414976 A | 11/1975 | | WO | WO 03/084357 | 8/2003 |
| GB | 2173496 A | 10/1986 | | WO | WO 2004/056758 | 7/2004 |
| GB | 2336584 A | 10/1999 | | WO | WO 2005021476 A1 | 3/2005 |
| HU | 2002-003023 | 3/2004 | | WO | WO 2005054167 A1 | 6/2005 |
| JP | 3927230 B2 | 11/1939 | | WO | WO 2005/097722 | 10/2005 |
| JP | 50-062909 | 5/1975 | | WO | WO 2005/115954 | 12/2005 |
| JP | 51021635 B | 7/1976 | | WO | WO 2005/116004 | 12/2005 |
| JP | 55041858 A | 3/1980 | | WO | WO 2006020234 A1 | 2/2006 |
| JP | 5629572 | 3/1981 | | WO | WO 2006/100311 A2 | 9/2006 |
| JP | 5699432 | 8/1981 | | WO | WO 2006/100312 A2 | 9/2006 |
| JP | 56-155009 | 12/1981 | | WO | WO 2006/100313 A2 | 9/2006 |
| JP | 60-258171 | 12/1985 | | WO | WO 2006/100314 A1 | 9/2006 |
| JP | 61-044833 | 3/1986 | | WO | WO 2006/100315 A2 | 9/2006 |

| | | | |
|---|---|---|---|
| WO | WO 2006/100316 A1 | 9/2006 |
| WO | WO 2006/100317 A1 | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO2008/107468 | 9/2008 |
| WO | WO2008/145729 | 12/2008 |
| WO | WO 2008/147473 | 12/2008 |
| WO | WO 2008/152043 | 12/2008 |
| WO | WO 2008/152045 | 12/2008 |
| WO | WO 2008/162044 | 12/2008 |
| WO | WO 2009/000773 | 12/2008 |
| WO | WO 2009/016149 A2 | 2/2009 |
| WO | WO2009026212 A1 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO2009/121853 A1 | 10/2009 |
| WO | WO 2009/121863 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |
| WO | WO 2012/016872 | 2/2012 |

OTHER PUBLICATIONS

U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al., unpublished.
U.S. Appl. No. 60/734,636, filed Nov. 8, 2005.
U.S. Appl. No. 11/915,088, filed Nov. 20, 2007, Krafft, et al., unpublished.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/529,777, filed Sep. 3, 2009, Krafft, et al.
U.S. Appl. No. 12/527,538, filed Aug. 17, 2009, Gilbeau et al.
U.S. Appl. No. 12/600,018, filed Nov. 13, 2009, Borremans.
U.S. Appl. No. 12/663,749, filed Dec. 9, 2009, Krafft, et al.
U.S. Appl. No. 12/663,753, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
Medium and Long-Term Opportunities and Risks of the Biotechnologial, Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).
Ullmann Encyl. Industr. Chem., $5^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55, 1984.
E. Milchert et al., "Installation for the Recovery of Dichloropropanols and Epichlorhydrin from the Waste Water in Epichlorhydrin Production", Pol. J. Appl. Chem., vol. 41, p. 113-118 (1997).
Kielboehmer W., et al, Solvay Werk Rheinberg: Integrierte Prozesse Seperierte Abwasserbehandlungen—Gewaesserschutz, Wasser, Abwasser 200 (Wissenschaftilch-technische Mitteilungen des Institute Zur Foerderung der Wasserguerte- und Wassermengenwirtschaft e; V;—2005 p. B1/B/5., vol. 5.
Klaus Weissermel, et al., "Industrial Organic Chemistry," ($3^{rd}$ Completely Revised Edition); VCH 1997, p. 93-98.
Klaus Weissermel, et al., "Industrial Organic Chemistry," ($3^{rd}$ Completely Revised Edition); VCH 1997, p. 276-277.
Klaus Weissermel, et al., "Industrial Organic Chemistry," ($3^{rd}$ Completely Revised Edition); VCH 1997, p. 347-355.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Attached Application No. FR 06.05325 filed Jun. 14, 2006 by Solvay S.A.—priority document to EP2007/55742 published as WO 2007/144335 (attached herein) 17 pgs.
Attached Application No. FR 07.53863 filed Mar. 15, 2007 by Solvay S.A. and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono- et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.

Rudnenko, EV, et al., 1988, Lakokrasochnye Materially i Ikh Primenenie, 4 69-71 (CA Summary) XP 002465276, 1 pg.

Kirk-Othmer Encyclopedia of Chemical Technology, 1978, 3rd Ed., vol. 4, Blood, Coagulants and Anticoagulants to Cardiovascular Agents. p. 847-848.

Jeffrey Lutje Spelberg, et al, A Tandem Enzyme Reaction to Produce Optically Active Halohydrins, Epoxides and Diols, Tetrahedron: Asymmetry, Elsevler Science Publishers, vol. 10, No. 15, 1999, pp. 2863-2870.

Oleoline.com. Glycerine Market report, Sep. 10, 2003, No. 62, 31 pgs.

Notification Under Act. No. 100/2001, Coll. As Amended by Act No. 93/2004, Coll. To the extent of Annex No. 4 (SPOLEK) Nov. 30, 2004, 80 pgs.

Documentation Under Act. No. 100/2001 Coll. As Amended by Act. No. 93/2004 Coll in the scope of appendix No. 4 (SPOLEK) Jan. 11, 2005, 86 pgs.

K. Weissermel & H.J. Arpe, Industrial Organic Chemistry, Third, Completely Revised Edition, VCH, 1997, pp. 149 & 275.

Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & Sons, Inc.

Ullmann's Encyclopedia of Industrial Chemistry, Fifth, Completely Revised Edition, 1988, vol. A13, pp. 292-293.

The Merck Index, Eleventh Edition, 1989, pp. 759-760.

Ullmann's Encyclopedia of Industrial Chemistry, Fifth completely Revised Edition, vol. A1, 1985, pp. 427-429.

Ullmann's Encyclopedia of Industrial Chemistry, Fifth Completely Revised Edition, vol. A6, 1986, pp. 240-252.

Hancock, E.G., Propylene and its Industrial Derivatives, 1973, pp. 298-332.

K. Weissermel & H.J. Arpe, Industrial Organic Chemistry, Third, Completely Revised Edition, VCH 1997, pp. 149-163.

K. Weissermel & H.J. Arpe, in Industrial Organic Chemistry, Third, Completely Revised Edition, VCH 1997, pp. 275-276.

Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (similar passages but retrieved from the English Fifth Edition of the Book, 1987).

Perry's Chemical Engineers' Handbook, Sixth Edition, Robert H. Perry, Don Green, 1984, Section 21-64 to 21-68.

Iwanami et al, Dictionary of Physics and Chemistry, Third Edition, Ryo Midorikawa /Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.

Kirk Othmer Encyclopedia of Chemical Technology, Third Edition, vol. 12, 1980, pp. 1002-1005.

Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.

Product Brochure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.

Berichte Der Deutschen Chemischen Gesellschaft, 1891, vol. 24, pp. 508-510.

Catalogue of Nittetu Chemical Engineering Ltd. (Published in Mar. 1994).

12093 Chemicals, The Chemical Daily Co., Ltd. (Published on Jan. 22, 1993) with attached English translation of relevant excerpts, 24 pgs.

Chemicals Guide, Chemical Daily Co., Ltd. (Published on Jun. 15, 1990) with attached English translation of relevant excerpts.

J.B. Conant, et al, "Glycerol a,y-dichlorohydrin", Organic Syntheses Coll., 1941, vol. 1, p. 292-294 (5 pp.).

"Epoxy resins", p. 36-46, by Shangai Resin Plant, Shangai People's Press, 1971—attached English translation only.

Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.

"Rainwater Harvesting and Utilization" (United Nations Environment Program) Mar. 2002; XP003003726; Internet Citation extracted online on Jan. 1, 2006: URL:http://www.unep.or.ip/letc/Publication—4 pp.

Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.

Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.

Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.

Laine, D.F. et al. "The destruction of organic pollutants under mild reaction conditions; A review" Michochemical Journal, vol. 85, No. 2, 2007 pp. 183-193; available online Aug. 17, 2006; 12 pp.

Horsley, Lee H.—"Azeotropic Data-III", The Dow Chemical Co., Midland, MI, American Chemical Society 1973; pp. 1-4; 4 pgs.

Suzawa, Yoshikazu, et al—"Incineration System for Waste Liquid Containing Chlorinated Organic Compounds", Chemical Apparatuses, 1981, vol. 23, No. 11; 34 pgs; Translation in English provided.

D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.

Chemical Engineering Handbook, $6^{th}$ Revised Edition, 2001, pp. 1-36; 56 pgs; Translation in English provided.

"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n°2, pp. 32-37, published Dec. 31, 1981; 17 pgs; Translation in English provided.

Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.

Encyclopedia of Chemical Technology, vol. 5, Nov. 1993; 6 pgs; Translation in English provided.

"Manufacture and use of epoxy resin", edited by Shanghai Resin Factory, published by China Petrochemical Press, First Edition, Oct. 1974; 16 pgs; Translation in English provided.

Gilman, Henry, et al—"Organic synthesis", Part 1, published by Scientific Publishing, 1957 (with abstract); 4 pgs.

Handbook of Chemical Products, Heavy Organic Chemicals, Second edition, published by Chemical Industry Press, Jan. 1995; 13 pgs; Translation in English provided.

Kiseleva, R. A., et al—"Study of the Interaction of Dibasic Acids with Glycerol", J. App. Chem. USSR, 1971, vol. 44, pp. 2086-2090; 5 pgs.

Handbook of Corrosion Data and Material Selection, published by Chemical Industry Press, edited by Jingyi Zuo, Yu Zuo; First edition, Oct. 1995, 5 pgs; Translation in English provided.

Handbook of Azeotropic Mixture, edited by Information Department of Comprehensive Scientific Technology Research Institution of Fushun City, 1993; 8 pgs; Translation in English provided.

"Industry Chemical Reaction and Application", published by Chinese Scientific Technology University Press, 1999; 4 pgs; Translation in English provided.

"Epoxy resin", published by Shanghai People's Publishing House, 1971; Translation in English provided; 21 pgs.

Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.

Encyclopedia for Chinese Adult Education, 1994, p. 623; 10 pgs; Translation in English provided.

[Unknown Author]—New Experimental Chemical Course 1, Basic Operation I, Section 4, Separation and Purification, pp. 251-252 (issued on Sep. 20, 1975) with English translation from Shiga International Patent Office, 3 pgs.

March, Jerry—"Reactions, Mechanisms & Structure", Advanced Organic Chemistry, 4$^{th}$ Ed., 1992, pp. 889, 908 and 937; 5 pgs.

[Unknown Author]—Bulletin de la Société Chimique de Paris—"Analyse des Travaux de Chimie Pure et Appliquée", G. Masson, Editor, Paris, Jul. 4, 1873, Novelle Série, Tome XIX, pp. 97-99; 4 pgs; comments regarding Friedel & Silva's work on middle of p. 98.

Neuberg, Irene Stephanie—"A New Way of Preparing Glyceraldehyde from Glycerol", Kaiser Wilhelm Institute in Berlin for Biochemi-Dahlem, 1930; 3 pgs; Includes abstract in English.

Krausz, Francois—'Recherches sur les Aldehydes Substitues en α en β. α and β Substituted Aldehydes', University Strasbourg, France ; Ann Chim 12, Nov.-Dec. 1949, 4, pp. 811-831, 23 pgs ; Includes abstract in English.

[Unknown Author]—"Glycerine—An Overview"—by The Soap and Detergent Association, Glycerine and Oleochemical Division, 1990; 27 pgs.

[Unknown Author]—"Commercial Synthesis of Glycerol Begins a New Shell Chemical Corp Plant—A staff Report"; Chemical & Engineering News, 1948, vol. 26, No. 38, pp. 2770-2771; 2 pgs.

Fairbourne, Arthur, et al—"The Partial Esterification of Polyhydric Alcohols . Part XII . The Funstion of Ethylene-oxide Rings", J. Chem. Soc. 1932, republished 1965, pp. 1965-1972; 8 pgs.

Clarke, H.T., et al—"Epichlorohydrin", Organic Syntheses, Coll. vol. 1, pp. 233 (1941) ; vol. 3, p. 47 (1923); 2 pgs.

Braun, Geza—"Epichlorohydrin and Epibromohydrin", Organic Syntheses, Coll. vol. 2, p. 256 (1943) ; vol. 16, p. 30 (1936); 2 pgs.

Conant, J.B., et al—"Glycerol α,γ-Dichlorohydrin", Organic Syntheses, Coll. vol. 1, p. 292 (1941); vol. 2, p. 29 (1922); 3 pgs.

Chavanne, G.—"Memoires Presentes a La Societe Chimique", English translation—"Reports Submitted to Chemical Firm", Bull. Soc. Chim. Fr. 1943, 1, EP 06 121 086; 16 pgs.

Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.

[Unknown Author]—"Chemical Properties and Derivatives of Glycerol", 1965, Glycerine Producer's Association, 1$^{st}$ Edition, 23 pgs.

Busby, G.W., et al—"The Purification of Glycerin by Ion-Exchange", The Journal of the American Oil Chemists' Society, 1952, 3 pgs.

Lamborn, Leebert Lloyd—"Modern Soaps, Candles and Glycerin", 3$^{rd}$ Edition, 1918, D. Van Nostrand Company, London, 12 pgs.

Knothe, Gerhard—"Historical perspectives on vegetable oil-based diesel fuels", Industrial Oils, 2001, vol. 12, pp. 1103-1107; 5 pgs.

Schuchardt, Ulf, et al—"Transesterification of Vegetable Oils: A Review", 1998, Braz. Chem Soc., vol. 9, No. 1, pp. 199-210; 12 pgs.

Claude, Sylvain—"Research of new outlets of glycerol—recent developments in France"—1999, Fett/Lipid, No. 3, Wiley-VCH Verlag GmbH, Weinheim, pp. 101-104; 4 pgs.

Prakash, Chandra B.—"A Critical Review of Biodiesel as a Transportation Fuel in Canada", 1998, GCSI—Global Change Strategies International Inc.; 119 pgs.

Fukuda, Hideki, et al—"Review—Biodiesel Fuel Production by Transesterification of Oils", 2001, Journal of Bioscience and Bioengineering; vol. 92, No. 5, pp. 405-416; 12 pgs.

Yong, K.C., et al—"Refining of Crude Glycerine Recovered From Glycerol Residue by Simple Vacuum Distillation", Dec. 2001, Journal of Oil Palm Research, vol. 13, No. 2, pp. 39-44, 6 pgs.

[Unknown Author], Kirk Othmer Encyclopedia of Chemical Technology—vol. 2, p. 156, John Wiley and Sons, 1992.

U.S. Appl. No. 12/681,083, filed Mar. 31, 2010, Bobet, et al.

U.S. Appl. No. 13/131,516, Patrick Gilbeau.

U.S. Appl. No. 13/060,421, filed Feb. 23, 2011, Dominique Balthasart et al.

U.S. Appl. No. 13/063,230, filed Mar. 10, 2011, Philippe Krafft et al.

Ma Zengxin et al, "Recovery of Polyglycerol from residues of Synthetic Glycerol" Riyong Huaxue Gongye, 1997, 4, 21023 (English Abstract only).

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.

Production and Prospect of the World Natural Glycerol by Zhu Shiyong, Cereals and Oils, vol. 1, 1997, pp. 33-38 (No English Translation).

Vinnolit: Vinnolit receives EU grant for water recycling project: Press Release, 2008: http://www.vinnolit.de/vinnolit.nsf/id/EN__Vinnolit_receives_EU_grant_for_water_recycling_project_.

N.W. Ziels, Journal of American Oil Chemists' Society, Nov. 1956, vol. 33, pp. 556-565.

Perry's Chemical Engineers Handbook, Sixth Edition. McGraw Hili Inc., (1964) Section 18.

vol. 83: Unit Operations II of Ullmann's Encyclopedia of Industrial Chemistry, Fifth Completely Revised Edition, Published by VCH, 1988.

W. Giger et al., "14C/12C—Ratios in Organic Matter and Hydrocarbons Extracted from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-876, XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

U.S. Appl. No. 12/745,802, Patrick Gilbeau, et al.

RD 436093, Aug. 10, 2000, Akzo Nobel.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

U.S. Appl. No. 12/864,211, filed Jul. 27, 2010, Patrick Gilbeau, et al.

Encyclopedia of Experimental Chemistry I, Basic Operation I, edited by the Chemical Society of Japan, Maruzen Co., Ltd., Nov. 5, 1990, 4th Edition, pp. 161 to 165 and 184 to 191 (no English translation available.

Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312 and 313 (no English translation available).

Clarke et al., Org Synth., Coll. vol. 1, p. 233-234, 1964.

Braun, Org. Synth., Coll., vol. 2, p. 256-259, 1957.

Kirk Othmer Encyclopedia of Chemical Technology, 3rd Edition, vol. 9, pp. 267-289, 1980.

Trent et al., "Reactive Stripping in a Rotating Packed Bed for the Production of Hypochlorous Acid", *BHR Group*, Conference Series Publication (1999), 38 (Process Intensification for the Chemical Industry), 217-231.

M. Vajda et al., Membrane-Based Extraction Joined with Membrane-Based Stripping in a Circulating Arrangement II. Extraction of Organic Acids, *Chemical Papers*, (2003), 57(1), 3-10.

U.S. Appl. No. 13/623,979, filed Sep. 21, 2012, Gilbeau.

U.S. Appl. No. 13/755,236, filed Jan. 31, 2013, Krafft, et al.

U.S. Appl. No. 13/709,218, filed Dec. 10, 2012, Boulos, et al.

U.S. Appl. No. 13/813,348, filed Jan. 30, 2013, Gilbeau, et al.

PROCESS FOR THE MANUFACTURE OF DICHLOROPROPANOL

CROSS-REFERENCE TO RELATED APPLICATIONS

The present patent application is a U.S. national stage application under 35 U.S.C. §371 of International Application No. PCT/EP2008/052972 filed Mar. 13, 2008, which claims the benefit of the French patent application No. FR 0753837 filed on Mar. 14, 2007, and of the provisional US patent application No. 61/013707 filed on Dec. 14, 2007, the content of both of which is each of these applications being incorporated herein by reference for all purposes.

The present invention relates to a process for manufacturing dichloropropanol. The present invention relates more specifically to a process for manufacturing dichloropropanol via reaction between glycerol and pressurized hydrogen chloride.

Dichloropropanol is a reaction intermediate in the manufacture of epichlorohydrin and epoxy resins (*Kirk-Othmer Encyclopedia of Chemical Technology*, Fourth Edition, 1992, Vol. 2, page 156, John Wiley & Sons, Inc.).

According to known processes, dichloropropanol can be obtained in particular by hypochlorination of allyl chloride, by chlorination of allyl alcohol and by chlorodehydroxylation of glycerol. The latter process exhibits the advantage that the dichloropropanol can be obtained starting from fossil raw materials or renewable raw materials and it is known that petrochemical natural resources, from which the fossil materials originate, for example oil, natural gas or coal, available on Earth are limited.

International Application WO 2006/020234 describes a process for manufacturing dichloropropanol via reaction between glycerol and gaseous hydrogen chloride under a superatmospheric partial pressure. Under such conditions, it is expected that it be difficult to separate the reaction products such as water and dichloropropanol, raw materials that have not reacted, including hydrogen chloride, and reaction intermediates, and that it be especially difficult to obtain dichloropropanol free from hydrogen chloride, with, as a consequence, a significant loss of this raw material.

The present invention aims to solve this problem by providing a novel process which prevents the contamination of dichloropropanol with hydrogen chloride and makes it possible to separate the reaction products, water and dichloropropanol, and the raw materials that have not reacted.

The invention hence relates to a process for manufacturing dichloropropanol according to which:
a) in a liquid reaction medium containing water, in contact with a gaseous phase, glycerol is reacted with hydrogen chloride under a partial pressure of hydrogen chloride in the gaseous phase greater than 0.2 bar absolute; and
b) at least part of the liquid reaction medium and optionally part of the gaseous phase from step a) is (are) subjected to at least one separation operation and, prior to said separation operation, the part of the liquid reaction medium and the part of the gaseous phase from step a) are subjected to:
  i. at least one treatment for reducing the weight ratio between the hydrogen chloride and the water in the part of the liquid reaction medium so as to attain a ratio less than or equal to the weight ratio between the hydrogen chloride and the water in the binary azeotropic hydrogen chloride/water composition at total pressure of the separation operation; and/or
  ii. at least one treatment for reducing the weight ratio between the water and the dichloropropanol in the part of the liquid reaction medium so as to attain a ratio less than or equal to the weight ratio between the water and the dichloropropanol in the ternary water/dichloropropanol/hydrogen chloride azeotrope at total pressure of the separation operation.

A first main feature of the present invention lies in the fact that at the end of the treatment from step bi) of the process, the weight ratio between the hydrogen chloride and the water in the liquid reaction medium is less than or equal to the weight ratio between the hydrogen chloride and the water in the binary azeotropic hydrogen chloride/water composition at total pressure of the separation operation. This ratio is 0.25 at a pressure of 1 bar absolute. The weight ratio between the hydrogen chloride and the water in the liquid reaction medium at the end of the treatment i) is preferably less than 0.95 times the weight ratio between the hydrogen chloride and the water of the binary azeotropic water/hydrogen chloride composition at total pressure of the separation operation and more preferably less than or equal to 0.9 times the latter weight ratio.

The weight ratio between the hydrogen chloride and the water in the binary azeotropic hydrogen chloride/water composition varies with pressure as shown by the liquid/vapour equilibrium data for the binary azeotropic hydrogen chloride/water composition given in Table 1 below:

TABLE 1

| Pressure (bar absolute) | Temperature (° C.) | HCl in azeotrope (g HCl/100 g azeotrope) | HCl/water in azeotrope (g/g) |
|---|---|---|---|
| 0.067 | 48.74 | 23.42 | 0.305 |
| 0.333 | 85.21 | 21.88 | 0.280 |
| 0.493 | 90.24 | 21.37 | 0.272 |
| 0.720 | 99.65 | 20.92 | 0.265 |
| 1 | 110 | 20 | 0.25 |
| 2 | 129 | 18 | 0.22 |
| 3 | 142 | 16 | 0.19 |
| 5 | 159 | 14 | 0.16 |
| 10 | 185 | 11 | 0.12 |
| 30 | 236 | 5 | 0.05 |
| 50 | 265 | 3 | 0.05 |

The values of 0.067 to 0.720 bar are taken from Bonner and Titus (J. Amer. Chem. Soc. 52, 633, (1930)). The values of 1 to 50 bar were calculated using the ASPEN+ calculation programme.

A second main feature of the present invention lies in the fact that at the end of the treatment from step bii) of the process, the weight ratio between the water and the dichloropropanol in the liquid reaction medium is less than or equal to the weight ratio between the water and the dichloropropanol in the ternary water/dichloropropanol/hydrogen chloride azeotrope at total pressure of the separation operation. This ratio is 1.6 at a pressure of 1 bar absolute. The weight ratio between the water and the dichloropropanol in the liquid reaction medium at the end of the treatment from step bii) is preferably less than 0.95 times the weight ratio between the water and the dichloropropanol in the ternary water/dichloropropanol/hydrogen chloride azeotrope at the product separation pressure, more preferably less than or equal to 0.9 times and most particularly preferably less than or equal to 0.8 times the latter weight ratio.

It has been discovered that, under these conditions, it is possible to recover dichloropropanol free from hydrogen chloride with the following advantages:
1. the dichloropropanol may be used in subsequent reactions such as the manufacture of epichlorohydrin for example, while avoiding:

a. overconsumption of basic agent; and
b. loss of recoverable hydrogen chloride;
2. limitation of corrosion phenomena in the processes of transfer and storage of dichloropropanol.

The expression "dichloropropanol free from hydrogen chloride" is understood to mean dichloropropanol of which the hydrogen chloride content is less than or equal to 5 g/kg of dichloropropanol, preferably less than or equal to 0.5 g/kg, more preferably less than or equal to 0.05 g/kg and most particularly preferably less than or equal to 0.005 g/kg.

In the process according to the invention, the total pressure of the reaction from step a) is generally at least 1 bar absolute, preferably at least 3 bar absolute, more preferably at least 5 bar absolute and most particularly preferably at least 10 bar absolute. It is at most 50 bar absolute and preferably at most 30 bar absolute.

In the process according to the invention, the partial pressure of the hydrogen chloride from step a) is preferably at least 0.4 bar absolute, more preferably at least 1 bar absolute, more preferably still at least 2 bar absolute and most particularly preferably at least 5 bar absolute. It is at most 50 bar absolute and preferably at most 30 bar absolute.

In the process according to the invention, the total pressure of the separation operation from step b) is generally less than or equal to the total pressure of the reaction from step a).

In the rest of the document, the expressions "pressure" and "total pressure" will be used indifferently to denote the total pressure.

In a first embodiment of the process according to the invention, the treatment from step bi) comprises an operation chosen from the operations of evaporation, distillation and stripping of the part of the liquid reaction medium from step a), and combinations of at least two of them.

In a first variant of the first embodiment, the treatment comprises an evaporation operation. The term "evaporation" is understood to mean the separation of a substance by heating, optionally under a reduced pressure. The temperature of the part of the liquid reaction medium from step a) during the evaporation operation is generally at least 70° C., usually at least 90° C., frequently at least 110° C. and more specifically at least 120° C. This temperature is generally at most 160° C., usually at most 150° C., frequently at most 140° C. and more specifically at most 130° C. This temperature is preferably above the reaction temperature of step a) if the pressure of the evaporation operation is higher than to the reaction pressure of step a). This temperature is preferably lower than or equal to the reaction temperature of step a) if the pressure of the evaporation operation is lower than or equal to the reaction pressure of step a). The evaporation operation may be carried out using any equipment such as, for example, a still, a natural circulation, rising film, falling film or rising and falling film or forced circulation tubular evaporator, or a plate evaporator. In this first variant, the evaporation may be carried out under a pressure of 1 bar absolute, under a pressure above 1 bar absolute or under a pressure below 1 bar absolute. It is preferred to carry out the evaporation under a pressure of at most 1.1 bar absolute. A simple means of carrying out the evaporation operation consists in bringing the part of the liquid reaction medium from step a) to atmospheric pressure by simple venting of this part to the atmosphere. In this first variant, the evaporation operation may be carried out in the presence or absence of a gas flow. It is preferred to carry out the evaporation under a gas flow.

In a second variant of the first embodiment, the treatment comprises a distillation operation. The term "distillation" is understood to mean the direct transition from the liquid state to the gas state, then condensation of the vapours obtained.

The term "fractional distillation" is understood to mean a series of distillations carried out on the successively condensed vapours. The fractional distillation treatment is preferred. In this second variant, the temperature of the part of the liquid reaction medium from step a) is generally at least 70° C., usually at least 90° C., frequently at least 110° C. and more specifically at least 120° C. This temperature is generally at most 160° C., usually at most 150° C., frequently at most 140° C. and more specifically at most 130° C. This temperature is preferably higher than or equal to the reaction temperature of step a) if the pressure of the distillation operation is higher than or equal to the reaction pressure of step a). This temperature is preferably below the temperature of step a) if the pressure of the distillation operation is lower than the reaction pressure of step a). In this second variant, the distillation may be carried out under a pressure of 1 bar absolute, under a pressure above 1 bar absolute or under a pressure below 1 bar absolute. It is preferred to carry out the distillation under a pressure of at most 1.5 bar absolute. The distillation operation may be carried out using any equipment such as, for example, a conventional plate column or a "dual-flow" type plate column, or else a column with random or structured packing. In this second variant, the distillation operation may be carried out in the presence or absence of a gas flow. It is preferred to carry out the distillation without a gas flow.

In a third variant of the first embodiment, the treatment comprises a stripping operation. The term "stripping" is understood to mean the separation of a substance by entrainment using the vapour of a material that does not dissolve this substance. In the process according to the invention, this material can be any compound which is inert with respect to dichloropropanol such as, for example, steam, air, nitrogen and carbon dioxide. It is preferred to use nitrogen, preferably relatively dry nitrogen, that is to say having a water content of at most 1000 ppm by weight. In this third variant, the temperature of the part of the liquid reaction medium from step a) is generally at least 70° C., usually at least 90° C., frequently at least 110° C. and more specifically at least 120° C. This temperature is generally at most 160° C., usually at most 150° C., frequently at most 140° C. and more specifically at most 130° C. This temperature is preferably higher than or equal to the reaction temperature of step a) if the pressure of the stripping operation is higher than or equal to the reaction pressure of step a). This temperature is preferably below the temperature of step a) if the pressure of the stripping operation is lower than the reaction pressure of step a). In this third variant, the stripping may be carried out under a pressure of 1 bar absolute, under a pressure above 1 bar absolute or under a pressure below 1 bar absolute. It is preferred to carry out the stripping under a pressure of at most 1.1 bar absolute.

In a fourth variant of the first embodiment according to the invention, the stripping and distillation treatments are combined, for example in a stripping column surmounted by a distillation section.

In the first embodiment of the process according to the invention, at the end of the treatment from step bi), a first fraction comprising at least 80 wt % of hydrogen chloride and a second fraction comprising dichloropropanol are recovered, the latter containing at most 30 wt % of hydrogen chloride, preferably at most 20 wt % of hydrogen chloride and particularly preferably at most 10 wt % of hydrogen chloride.

The hydrogen chloride from the first fraction preferably contains at most 10 wt % of water and most particularly preferably at most 5 wt %. The hydrogen chloride may be recycled to step a) of the process according to the invention or be used in any other process.

In a second embodiment of the process according to the invention, the treatment from step bi) comprises an operation chosen from the operations of addition of glycerol and/or glycerol esters, and/or of monochloropropanediol and/or monochloropropanediol esters and/or of a basic agent to the part of the liquid reaction medium from step a).

In a first variant of the second embodiment of the process according to the invention, the treatment from step bi) comprises the operation of addition of glycerol to the part of the liquid reaction medium from step a).

The glycerol in the process according to the invention may be obtained starting from fossil raw materials or starting from renewable raw materials, preferably starting from renewable raw materials.

The expression "fossil raw materials" is understood to mean materials derived from the treatment of petrochemical natural resources, for example oil, natural gas and coal. Among these materials, organic compounds that consist of a number of carbon atoms which is a multiple of 3 are preferred. Allyl chloride, allyl alcohol and "synthetic" glycerol are particularly preferred. The term "synthetic" glycerol is understood to mean a glycerol generally obtained from petrochemical resources.

The expression "renewable raw materials" is understood to mean materials derived from the treatment of renewable natural resources. Among these materials, "natural" glycerol is preferred. "Natural" glycerol may, for example, be obtained by conversion of sugars via thermochemical processes. These sugars may possibly be obtained starting from biomass, as described in "Industrial Bioproducts: Today and Tomorrow, Energetics, Incorporated for the U.S. Department of Energy, Office of Energy Efficiency and Renewable Energy, Office of the Biomass Program, July 2003, pages 49, 52 to 56". One of these processes is, for example, catalytic hydrogenolysis of sorbitol obtained by thermochemical conversion of glucose. Another process is, for example, catalytic hydrogenolysis of xylitol obtained by hydrogenation of xylose. Xylose may, for example, be obtained by hydrolysis of hemicellulose contained in maize fibres. The expressions "natural glycerol" or "glycerol obtained from renewable raw materials" are understood to mean, in particular, glycerol obtained during the manufacture of biodiesel or else glycerol obtained during conversions of fats or oils of vegetable or animal origin in general such as saponification, transesterification or hydrolysis reactions.

Among the oils that can be used to manufacture natural glycerol, mention may be made of all common oils, such as palm, palm kernel, coconut, babassu, old or new rapeseed, sunflower, maize, castor and cottonseed oils, arachis, soybean, linseed and sea kale oils, all the oils derived from, for example, sunflower or rapeseed plants obtained by genetic modification or hybridization.

Use can even be made of used frying oils, various animal oils, such as fish oils, tallow, lard and even abattoir fats.

Among the oils used, mention may also be made of oils partially modified, for example, by polymerization or oligomerization such as, for example, the "stand oils" of linseed and sunflower oils and blown vegetable oils.

A particularly suitable glycerol may be obtained during the conversion of animal fats. Another particularly suitable glycerol may be obtained during the manufacture of biodiesel. Another particularly suitable glycerol may be obtained during the fatty acid manufacture.

In a first aspect of the first variant of the second embodiment of the process according to the invention, a glycerol external to the process according to the invention is used. The term "external" glycerol is understood to mean glycerol which is not recycled in the process according to the invention.

In a second aspect of the first variant of the second embodiment of the process according to the invention, a mixture of glycerol "external" to the process according to the invention and of glycerol "internal" to the process according to the invention is used. The term "internal" glycerol is understood to mean glycerol which has been separated from the reaction products formed in the process according to the invention and which has then been recycled in the process according to the invention.

In a second variant of the second embodiment, the treatment from step bi) comprises the operation of addition of glycerol esters to the part of the liquid reaction medium from step a).

The glycerol ester used in the process according to the invention may be obtained by any route, for example by reaction between glycerol and an organic acid. The organic acids preferred in the process according to the invention are the carboxylic acids used as chlorodehydroxylation catalysts for glycerol such as those described in the patent application in the name of Solvay SA (WO 2005/054167) and in Application WO 2006/020234.

In a first aspect of the second variant of the second embodiment of the process according to the invention, a glycerol ester external to the process according to the invention is used. The term "external" glycerol ester is understood to mean a glycerol ester which is not recycled in the process according to the invention.

In a second aspect of the second variant of the second embodiment of the process according to the invention, a glycerol ester "internal" to the process according to the invention is used. The term "internal" glycerol ester is understood to mean a glycerol ester which has been separated from the reaction products formed in the process according to the invention and which has then been recycled in the process according to the invention.

In a third aspect of the second variant of the second embodiment of the process according to the invention, a mixture of glycerol ester "external" to the process according to the invention and of glycerol ester "internal" to the process according to the invention is used.

In a third variant of the second embodiment of the process according to the invention, the treatment from step bi) comprises the operation of addition of monochloropropanediol to the part of the liquid reaction medium from step a).

The monochloropropanediol used in the process according to the invention may be obtained by any route, for example by reaction between glycerol and the chlorinating agent or by hydrolysis of epichlorohydrin.

In a first aspect of the third variant of the second embodiment of the process according to the invention, a monochloropropanediol external to the process according to the invention is used. The term "external" monochloropropanediol is understood to mean monochloropropanediol which is not one of the products formed in the process according to the invention.

In a second aspect of the third variant of the second embodiment of the process according to the invention, which is preferred, a monochloropropanediol internal to the process according to the invention is used. The term "internal" monochloropropanediol is understood to mean monochloropropanediol which is one of the products formed in the process according to the invention, which has been separated from the other reaction products and which has then been recycled in the process according to the invention.

In a fourth variant of the second embodiment of the process according to the invention, the treatment from step bi) comprises the operation of addition of monochloropropanediol ester to the part of the liquid reaction medium from step a).

The monochloropropanediol ester used in the process according to the invention may be obtained by any route, for example by reaction between the monochloropropanediol and an organic acid. The organic acids preferred in the process according to the invention are the carboxylic acids used as chlorodehydroxylation catalyst for glycerol such as those described in the patent application in the name of Solvay SA (WO 2005/054167) and in Application WO 2006/020234.

In a first aspect of the fourth variant of the second embodiment of the process according to the invention, a monochloropropanediol ester external to the process according to the invention is used. The term "external" monochloropropanediol ester is understood to mean a monochloropropanediol ester which is not one of the products formed in the process according to the invention.

In a second aspect of the fourth variant of the second embodiment of the process according to the invention, which is preferred, a monochloropropanediol ester internal to the process according to the invention is used. The term "internal" monochloropropanediol ester is understood to mean a monochloropropanediol ester which is one of the products formed in the process according to the invention, which has been separated from the other reaction products and which has then been recycled in the process according to the invention.

The glycerol, glycerol esters, monochloropropanediol and monochloropropanediol esters may be added as a mixture of two, three or four of these compounds.

In the aspects of the various variants of the second embodiment, which involve internal glycerol, internal glycerol esters, internal monochloropropanediol and internal monochloropropanediol esters, these compounds may be accompanied by other compounds, for instance impurities of the process, such as for example glycerol oligomers that are chlorinated and/or esterified to a greater or lesser extent.

Without wishing to be tied to one theoretical explanation, it is believed that in the various variants of the second embodiment of the process according to the invention, the glycerol and/or glycerol esters and/or monochloropropanediol and/or monochloropropanediol esters react with the hydrogen chloride present in the liquid reaction medium from step a) so as to generate at least dichloropropanol and/or dichloropropanol esters and/or monochloropropanediol and/or monochloropropanediol esters and water, with the following additional advantages: increase of the dichloropropanol yield, formation of a reaction intermediate that can be recycled after separation in step a) of the process according to the invention, and decrease of the hydrogen chloride/water ratio.

In these first, second, third and fourth variants of the second embodiment of the process according to the invention, the molar ratio of the amount of glycerol and/or glycerol esters and/or monochloropropanediol and/or monochloropropanediol esters to the amount of hydrogen chloride in the part of the reaction medium from step a) after addition of the glycerol and/or glycerol esters and/or monochloropropanediol and/or monochloropropanediol esters and before the optional reaction with the hydrogen chloride is generally at least 1 mol/mol, preferably at least 3 mol/mol and more particularly preferably at least 5 mol/mol.

In these first, second, third and fourth variants of the second embodiment of the process according to the invention, the treatment temperature is generally at least 60° C., usually at least 80° C., frequently at least 100° C. and more specifically at least 110° C. This temperature is generally at most 150° C., usually at most 140° C., frequently at most 130° C. and more specifically at most 120° C. This temperature is preferably higher than or equal to the reaction temperature of step a) if the pressure of the treatment is higher than or equal to the reaction pressure of step a). This temperature is preferably below the temperature of step a) if the pressure of the treatment is lower than the reaction pressure of step a). In these variants, the pressure may be 1 bar absolute, above 1 bar absolute or below 1 bar absolute. It is preferred to operate under a pressure of at most 1.2 bar absolute. In these variants, the treatment time is generally at least 15 min, preferably at least 30 min and particularly preferably at least 45 min. This time is at most 8 h, preferably at most 4 h and particularly preferably at most 2 h. The treatment may be carried out in batch mode in a mixed reactor or continuously in a plug-flow reactor or in a mixed reactor.

In a fifth variant of the second embodiment of the process according to the invention, the treatment from step bi) comprises the operation of addition of a basic compound to the part of the liquid reaction medium from step a).

In this fifth variant of the second embodiment of the process according to the invention, the basic compound may be an organic or inorganic basic compound. Organic basic compounds are for example amines, phosphines or arsines, preferably sterically hindered, and ammonium, phosphonium or arsonium hydroxides. Inorganic basic compounds are preferred. The expression "inorganic compounds" is understood to mean compounds which do not contain a carbon-hydrogen bond. The inorganic basic compound may be chosen from alkali and alkaline-earth metal oxides, hydroxides, carbonates, hydrogencarbonates, phosphates, hydrogenphosphates and borates, and mixtures thereof. Alkali and alkaline-earth metal oxides and hydroxides are preferred.

In this variant, the basic compound may be in the form of a liquid, an essentially anhydrous solid, a hydrated solid, an aqueous and/or organic solution or an aqueous and/or organic suspension. The basic compound is preferably in the form of an essentially anhydrous solid, a hydrated solid, an aqueous solution or an aqueous suspension.

The expression "essentially anhydrous solid" is understood to mean a solid of which the water content is less than 20 g/kg, preferably less than or equal to 10 g/kg and more preferably less than or equal to 1 g/kg.

The expression "hydrated solid" is understood to mean a solid of which the water content is at least 20 g/kg and at most 700 g/kg, preferably at least 50 g/kg and at most 650 g/kg and most particularly preferably at least 130 g/kg and at most 630 g/kg. The hydrates which denote solid combinations of substances with one or more water molecules are examples of hydrated solids.

When the basic compound is used in the form of an aqueous solution, its content in the aqueous solution is generally greater than 20 g/kg, preferably greater than or equal to 70 g/kg and more preferably greater than or equal to 150 g/kg. This content is generally less than or equal to the solubility of the basic solid in water at the temperature of the treatment from step bi).

When the basic compound is used in the form of an aqueous suspension, its content in the aqueous suspension is generally greater than the solubility of the basic solid in water at the temperature of the treatment from step bi), preferably greater than or equal to 20 g/kg and more preferably greater than or equal to 70 g/kg.

The preferred basic compounds are in the form of concentrated aqueous solutions or suspensions of sodium hydroxide or calcium hydroxide or in the form of purified caustic brine.

The expression "purified caustic brine" here means sodium hydroxide which contains sodium chloride such as, for example, that produced in a diaphragm electrolysis process. The sodium hydroxide content of the purified caustic brine is generally greater than or equal to 30 g/kg, preferably greater than or equal to 40 g/kg and more preferably greater than or equal to 60 g/kg. This sodium hydroxide content is generally less than or equal to 300 g/kg, preferably less than or equal to 250 g/kg and more preferably less than or equal to 200 g/kg. The sodium chloride content of the purified caustic brine is generally greater than or equal to 30 g/kg, preferably greater than or equal to 50 g/kg and more preferably greater than or equal to 70 g/kg. This sodium chloride content is generally less than or equal to 250 g/kg, preferably less than or equal to 200 g/kg and more preferably less than or equal to 180 g/kg.

Without wishing to be tied to one theoretical explanation, it is believed that in this fifth variant of the second embodiment of the process according to the invention, the basic compound reacts with the hydrogen chloride present in the liquid reaction medium from step a) so as to generate at least one salt and water, the water formed contributing to the reduction of the hydrogen chloride/water ratio. The salt generated in this variant may also have a salting-out effect with respect to the hydrogen chloride, that is to say contribute to reducing the solubility of hydrogen chloride in the liquid reaction medium.

In this fifth variant of the second embodiment of the process according to the invention, the molar ratio of the basic compound to the hydrogen chloride in the part of the reaction medium from step a) after addition of the basic compound and before the optional reaction with the hydrogen chloride is generally at least 0.4, preferably at least 0.6 and more particularly preferably at least 0.8.

In this fifth variant of the second embodiment of the process according to the invention, the treatment temperature is generally at least 60° C., usually at least 80° C., frequently at least 100° C. and more specifically at least 110° C. This temperature is generally at most 150° C., usually at most 140° C., frequently at most 130° C. and more specifically at most 120° C. This temperature is preferably higher than or equal to the reaction temperature of step a) if the pressure of the treatment is higher than or equal to the reaction pressure of step a). This temperature is preferably below the temperature of step a) if the pressure of the treatment is lower than the reaction pressure of step a). In this variant, the treatment pressure may be 1 bar absolute, above 1 bar absolute or below 1 bar absolute. It is preferred to operate under a pressure of at most 1.1 bar absolute. In this variant, the treatment time is generally at least 0.5 min, preferably at least 1 min and particularly preferably at least 2 min. This time is at most 60 min, preferably at most 30 min and particularly preferably at most 10 min. The operation may be carried out in batch mode or continuously in a plug-flow reactor or in a mixed reactor.

In a third embodiment of the process according to the invention, the treatment from step bi) comprises an operation chosen from the operations of addition of:
(A) water; or
(B) a dichloropropanol/water/hydrogen chloride mixture in which:
  1) the hydrogen chloride/water weight ratio is less than the weight ratio between the hydrogen chloride and the water in the binary azeotropic hydrogen chloride/water composition at total pressure of the separation operation; and/or
  2) the dichloropropanol/water weight ratio is less than the weight ratio between the water and the dichloropropanol in the ternary water/dichloropropanol/hydrogen chloride azeotrope at total pressure of the separation operation;
or
(C) a compound that forms an azeotrope with hydrogen chloride and water, and of which the boiling point is below the boiling point of the ternary water/dichloropropanol/hydrogen chloride azeotrope at total pressure of the separation operation; or
(D) a salt-out salt,
to the part of the liquid reaction medium from step a).

The boiling point of the ternary water/dichloropropanol/hydrogen chloride azeotrope is 106° C. under a pressure of 1 bar absolute and this boiling point varies with the pressure.

In a first variant of the third embodiment of the process according to the invention, the treatment from step bi) comprises the addition of water to the part of the liquid reaction medium from step a).

In a first aspect of the first variant of the third embodiment of the process according to the invention, water external to the process according to the invention is used. The term "external" water is understood to mean water which is not recycled in the process according to the invention.

In a second aspect of the first variant of the third embodiment of the process according to the invention, water "internal" to the process according to the invention is used. The term "internal" water is understood to mean water which has been separated from the reaction products formed in the process according to the invention and which has then been recycled in the process according to the invention.

In a third aspect of the first variant of the third embodiment of the process according to the invention, a mixture of water "external" to the process according to the invention and of water "internal" to the process according to the invention is used.

In a second variant of the third embodiment of the process according to the invention, the treatment from step bi) comprises the addition of a dichloropropanol/water/hydrogen chloride mixture in which the hydrogen chloride/water weight ratio is less than the weight ratio between the hydrogen chloride and the water in the binary azeotropic hydrogen chloride/water composition at total pressure of the separation operation. This ratio is preferably less than 0.25. This ratio is more preferably less than or equal to 0.15, even more preferably less than or equal to 0.1 and most particularly preferably less than or equal to 0.005.

In a first aspect of the second variant of the third embodiment of the process according to the invention, the dichloropropanol/water weight ratio in the dichloropropanol/water/hydrogen chloride mixture is greater than or equal to the weight ratio between the dichloropropanol and the water in the binary azeotropic dichloropropanol/water composition at total pressure of the separation operation. This ratio is preferably greater than or equal to 0.30. The weight ratio between the dichloropropanol and the water in the binary azeotropic dichloropropanol/water composition at a pressure of 1 bar absolute is 0.3.

In a second aspect of the second variant of the third embodiment of the process according to the invention, which is preferred, the dichloropropanol/water weight ratio in the dichloropropanol/water/hydrogen chloride mixture is less than the weight ratio between the dichloropropanol and the water in the binary azeotropic dichloropropanol/water composition at total pressure of the separation operation. This ratio is preferably at most 0.30, preferably at most 0.2, more preferably at most 0.1 and most particularly preferably at most 0.05.

In a third variant of the third embodiment of the process according to the invention, the treatment from step bi) comprises the addition of a compound that forms an azeotrope with hydrogen chloride and water, and of which the boiling point is below the boiling point of the ternary water/dichloropropanol/hydrogen chloride azeotrope at total pressure of the separation operation, which boiling point is 106° C. under a pressure of 1 bar absolute. This boiling point is preferably less than 104° C., more preferably less than or equal to 100° C. and most particularly preferably less than or equal to 98° C. Without being limiting, examples of such compounds which may be used include chlorobenzene, toluene, benzene, heptane and octane.

In a fourth variant of the third embodiment of the process according to the invention, the treatment from step bi) comprises the addition of a salt-out salt to the part of the liquid reaction medium from step a). The expression "salt-out salt" is understood to mean a salt which contributes to reducing the solubility of hydrogen chloride in the liquid reaction medium.

In a first aspect of the fourth variant of the third embodiment of the process according to the invention, a salt external to the process according to the invention is used. The term "external" salt is understood to mean a salt which is not recycled in the process according to the invention.

In a second aspect of the fourth variant of the third embodiment of the process according to the invention, a salt "internal" to the process according to the invention is used. The term "internal" salt is understood to mean a salt which has been separated from the reaction products formed in the process according to the invention and which has then been recycled in the process according to the invention. These salts may, for example, be present in the reactants, such as glycerol.

In a third aspect of the fourth variant of the third embodiment of the process according to the invention, a mixture of a salt "external" to the process according to the invention and of a salt "internal" to the process according to the invention is used.

The salt is preferably chosen from alkali and alkaline-earth metal halides, sulphates, hydrogensulphates, phosphates, hydrogenphosphates and borates, and mixtures thereof. Alkali metal halides and sulphates are preferred, sodium and potassium chlorides and sulphates being more preferred, sodium chloride being most particularly preferred.

Without wishing to be tied to any one theoretical explanation, it is believed that the addition of salt reduces the solubility of hydrogen chloride in the part of the liquid reaction medium from step a).

In a fourth embodiment of the process according to the invention, the treatment from step bi) comprises an operation chosen from the operations of adsorption and/or liquid/liquid extraction, the adsorption operation being preferred.

The adsorbents may be chosen from molecular sieves, preferably from molecular sieves having a pore size of at least 0.3 nm and at most 1 nm. Examples of such molecular sieves are type A or X molecular sieves. The molecular sieves are preferably acid-resistant.

Without wishing to be tied to any one theoretical explanation, it is believed that such compounds make it possible to adsorb hydrogen chloride from the part of the liquid reaction medium from step a).

At the end of the treatment from step bi), the adsorbent may be subjected to operations intended to separate the hydrogen chloride from the adsorbent, such as the operations of stripping or regeneration by heating. The thus separated hydrogen chloride may be recycled to step a) of the reaction and the thus separated adsorbent may be recycled to the treatment from step bi) of the process according to the invention.

In the four embodiments of the process according to the invention described above, the part of the reaction medium at the end of the treatment from step bi) may be subjected to at least one operation of separation by distillation, recovered at the end of which is a first portion (I) comprising dichloropropanol and water, said portion containing at most 20 g of hydrogen chloride/kg of portion; and
  a second portion (IIa) comprising hydrogen chloride, water and dichloropropanol, and a third portion (IIIa) containing dichloropropanol; or
  a second portion (IIb) comprising hydrogen chloride, water and dichloropropanol, and a third portion (IIIb) comprising hydrogen chloride and water; or
  a second portion (IIc) comprising hydrogen chloride and water, and a third portion (IIIc) containing water.

The first portion (I) preferably contains at most 15 g of hydrogen chloride/kg of mixture, preferably at most 10 g/kg and particularly preferably at most 1 g/kg. This mixture contains at least 1 ppm by weight of hydrogen chloride per kg of mixture. The first portion (I) contains from 10 to 26 wt %, preferably 23 wt %, of dichloropropanol, and from 74 to 90 wt %, preferably 77 wt %, of water, the weight percentages being relative to the sum of the weights of water and dichloropropanol in the first portion.

The second portion comprising hydrogen chloride, water and dichloropropanol (IIa, IIb) contains from 43 to 63 wt %, preferably 53 wt %, of water, from 23 to 43 wt %, preferably 33 wt %, of dichloropropanol and from 4 to 24 wt %, preferably 14 wt %, of hydrogen chloride, the weight percentages being relative to the sum of the weights of hydrogen chloride, water and dichloropropanol in the second portion.

The third portion (IIIa) containing dichloropropanol comprises at least 900 g of dichloropropanol per kg of said third portion, preferably at least 950 g/kg and more preferably at least 990 g/kg.

The second portion (IIc) and the third portion (IIIb), containing hydrogen chloride and water, contain from 18 to 22 wt %, preferably 20 wt %, of hydrogen chloride, and from 78 to 82 wt %, preferably 80 wt %, of water, the weight percentages being relative to the sum of the weights of water and hydrogen chloride in said second (IIc) and third (IIIb) portions.

The third portion (IIIc) containing water comprises at least 950 g of water per kg of said third portion (IIIc), preferably at least 990 g/kg and more preferably at least 995 g/kg.

These situations may be visualized in the ternary dichloropropanol/hydrogen chloride/water diagram from FIG. 1 where the peaks represent pure compounds, point D represents a ternary azeotropic dichloropropanol/hydrogen chloride/water composition, point E represents a binary azeotropic hydrogen chloride/water composition, point F represents a binary azeotropic dichloropropanol/water composition and point G is the intersection point between the dichloropropanol-water axis and a straight line comprising points A and D. For these particular compositions D, E, and F, the following will respectively be denoted: by (d), the weight ratio between dichloropropanol and water in composition D, by (e), the weight ratio between hydrogen chloride and water in composition E, by (f), the weight ratio between water and dichloropropanol in composition F.

Separation into the portions I, IIa and IIIa is obtained when the part of the reaction medium at the end of the treatment from step bi) has a dichloropropanol/hydrogen chloride/water composition which lies in the BDF zone of the diagram from FIG. 1.

Separation into the portions I, IIb and IIIb is obtained when the part of the reaction medium at the end of the treatment from step bi) has a dichloropropanol/hydrogen chloride/water composition which lies in the DEF zone of the diagram from FIG. 1.

Separation into the portions I, IIc and IIIc is obtained when the part of the reaction medium at the end of the treatment from step bi) has a dichloropropanol/hydrogen chloride/water composition which lies in the EFC zone of the diagram from FIG. 1.

In a fifth embodiment of the process according to the invention, the treatment from step bii) comprises an operation chosen from the operations of adsorption and/or liquid/liquid extraction.

The adsorption operation may be carried out using an adsorbent chosen from molecular sieves, preferably from molecular sieves having a pore size of at least 0.3 nm and at most 1 nm. Examples of such molecular sieves are type A or X molecular sieves. The molecular sieves are preferably acid-resistant.

The liquid/liquid extraction operation may be carried out using a semi-permeable membrane.

Without wishing to be tied to any one theoretical explanation, it is believed that such compounds make it possible to adsorb or to extract water or a mixture comprising water and hydrogen chloride from the part of the liquid reaction medium from step a).

At the end of the treatment from step bii), the adsorbent and the extraction liquid may be subjected to operations intended to separate the water and hydrogen chloride from the adsorbent or from the extraction liquid, such as the operations of evaporation, stripping or regeneration by heating. The thus separated hydrogen chloride may be recycled to step a) of the reaction and the thus separated adsorbent and extraction liquid may be recycled to step bii) of the process according to the invention.

In the fifth embodiment of the process according to the invention described above, the part of the reaction medium at the end of the treatment from step bii) may be subjected to at least one separation by distillation, recovered during which is at least a first part comprising dichloropropanol and a second part comprising hydrogen chloride.

This situation may be visualized in the ternary diagram of the dichloropropanol/hydrogen chloride/water composition from FIG. 1.

Separation into the parts respectively comprising dichloropropanol and hydrogen chloride is obtained when the part of the reaction medium at the end of the treatment from step bii) has a dichloropropanol/hydrogen chloride/water composition which lies in the ABD zone of the diagram from FIG. 1.

The first part containing dichloropropanol comprises at least 900 g of dichloropropanol per kg of said first part, preferably at least 950 g/kg and more preferably at least 990 g/kg.

The second part containing hydrogen chloride comprises at least 900 g of hydrogen chloride per kg of said second part, preferably at least 950 g/kg and more preferably at least 990 g/kg. This hydrogen chloride may be recycled to step a) of the process according to the invention.

The various embodiments described above may be combined together in any manner. Some of these combinations are described herein below.

Figure 2:
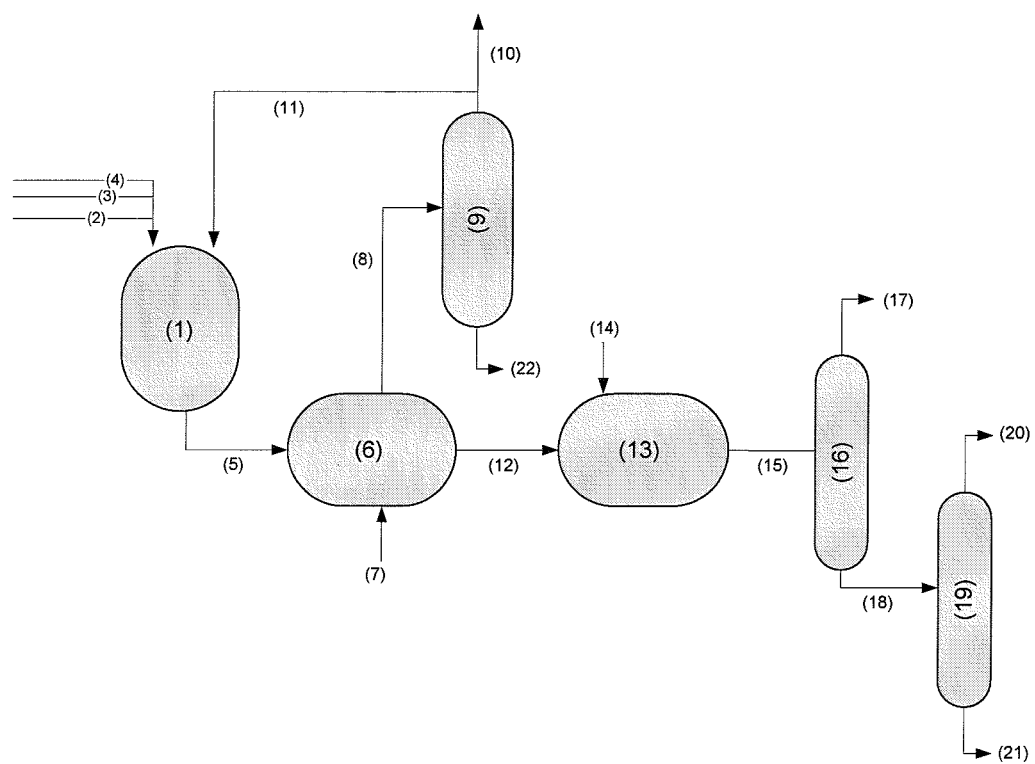

In a first combination of embodiments of the process according to the invention which is presented in FIG. 2, a first reactor (1) is continuously supplied with glycerol, gaseous hydrogen chloride and a catalyst respectively via the lines (2), (3) and (4). The reactor is permanently kept under a partial pressure of hydrogen chloride above 0.2 bar absolute. A liquid flow in which the weight ratio between the hydrogen chloride and the water is above (e) and the ratio between the dichloropropanol and the water is higher than (d) (ABD zone of the ternary diagram from FIG. 1) is continuously drawn off from the reactor (1) via the line (5) and supplies a stripping machine (6) in which the pressure is kept at less than 1 bar absolute and in which a flow of inert gas is introduced via the line (7). A gas flow containing hydrogen chloride is drawn off from the stripping machine (6) via the line (8) and supplies a distillation column (9). A flow containing hydrogen chloride, water and dichloropropanol in small amounts is drawn off from the column (9) via the line (10). One part of this flow is optionally recycled to the reactor (1) via the line (11). A flow containing a mixture of dichloropropanol, hydrochloric acid and water is drawn off from the bottom of the column (9) via the line (22). A liquid flow in which the weight ratio between the hydrogen chloride and the water is greater than or equal to (e) but less than its value in the flow drawn off in (5) and the ratio between the dichloropropanol and the water is higher than (d) (ABD zone of the ternary diagram from FIG. 1) is drawn off from the stripping machine (6) via the line (12) and supplies a container (13) in which a flow of glycerol and/or glycerol esters and/or monochloropropanediol and/or monochloropropanediol esters is introduced via the line (14). A liquid flow, of which the dichloropropanol/hydrogen chloride/water composition is in the BDG zone of the ternary diagram from FIG. 1, is drawn off from the container (13) via the line (15) and supplies a distillation column (16). A flow comprising water and dichloropropanol is drawn off from the top of the column (16) via the line (17). A flow comprising water, dichloropropanol and hydrogen chloride is drawn off from the bottom of the column (16) via the line (18). The line (18) supplies a distillation column (19). A flow comprising water, dichloropropanol and hydrogen chloride is drawn off from the top of the column (19) via the line (20). The flow from the line (20) may, completely or partly, be recycled to the reactor (1). A flow comprising dichloropropanol is drawn off from the bottom of the distillation column (19) via the line (21).

The dichloropropanol obtained in the flow (21) may be purified, for example by distillation, in order to eliminate the other compounds that constitute heavy compounds from the reaction medium, such as the catalyst, glycerol monochlorohydrin and chlorinated glycerol oligomers. The latter may be completely or partly recycled to the reactor (1).

In a second combination of embodiments of the process according to the invention, the same equipment as that which is presented in FIG. 2 is used, except that in the liquid flow which is continuously drawn off from the reactor (1) the weight ratio between the hydrogen chloride and the water is greater than (e) and the ratio between the dichloropropanol and the water is lower than (d) (ADE zone of the ternary diagram from FIG. 1) and in the liquid flow which is continuously drawn off from the container (13) the weight ratio between the water and the dichloropropanol and the weight ratio between the hydrogen chloride and the water are such that the dichloropropanol/hydrogen chloride/water composition is in the DGF zone of the ternary diagram from FIG. 1.

In a third combination of embodiments of the process according to the invention, the same procedure as in the second embodiment is followed, except that:
1) in the liquid flow which is continuously drawn off from the container (13) the weight ratio between the water and the dichloropropanol and the weight ratio between the hydrogen chloride and the water are such that the dichloropropanol/hydrogen chloride/water composition is in the DEF zone of the ternary diagram from FIG. 1; and 2) the flow drawn off from the bottom of the column (19) via the line (21) contains water and hydrogen chloride.

In a fourth combination of embodiments of the process according to the invention, the same procedure as in the second embodiment is followed, except that:

1) in the liquid flow which is continuously drawn off from the container (13) the weight ratio between the water and the dichloropropanol and the weight ratio between the hydrogen chloride and the water are such that the dichloropropanol/hydrogen chloride/water composition is in the EFC zone of the ternary diagram from FIG. 1;
2) the flow drawn off from the top of the column (19) via the line (20) contains water; and
3) the flow drawn off from the bottom of the column (19) via the line (21) contains water and hydrogen chloride.

Figure 3:
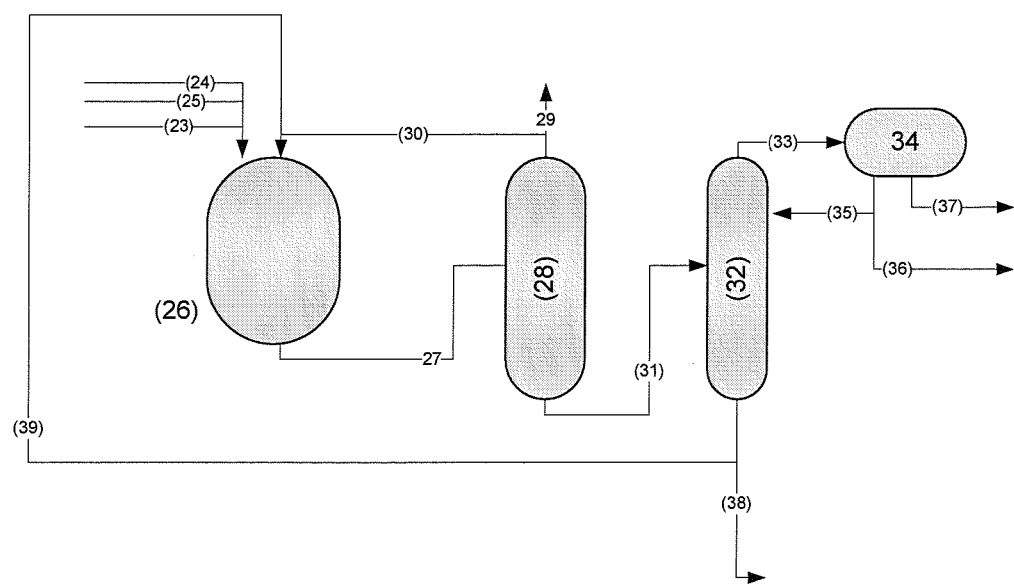

In a fifth combination of embodiments of the process according to the invention which is presented in FIG. 3, a first reactor (26) is continuously supplied with glycerol, gaseous hydrogen chloride and a catalyst respectively via the lines (23), (24) and (25). The reactor is permanently kept under a partial pressure of hydrogen chloride above the partial pressure of hydrogen chloride in the water/hydrogen chloride azeotrope at the reaction pressure. The total pressure is of 8 bar absolute.

A liquid flow is drawn off from the reactor (26) via the line (27). This flow supplies a column (28) kept at a pressure of 8 bar absolute, this column possibly being composed only of a single bottom section. Drawn off from the column (28) via the line (29) is a flow that is very rich in hydrogen chloride and that contains a little water and dichloropropanol. This flow may be completely or partly recycled to the reactor (26) via the line (30). Drawn off from the column (28) via the line (31) is a liquid flow containing most of the organic compounds, and also water and hydrogen chloride. The ratio of the weight concentration of hydrogen chloride relative to the water in the flow from the line (31) is 0.16, which corresponds to the weight ratio of hydrogen chloride in the water/hydrogen chloride azeotrope at a pressure of 8 bar absolute. The flow (31) supplies a distillation column (32) kept under a pressure of 0.1 bar absolute. A flow is drawn off from the top of the column (32) via the line (33). This flow supplies a settling tank (34) in which a light phase and a heavy phase are separated. The light phase is drawn off from the settling tank (34) via the line (36). A part of this light phase exiting the settling tank (34), which essentially contains water, is conveyed back to the column (32) via the line (35). The heavy phase is drawn off from the settling tank (34) via the line (37). This phase essentially contains dichloropropanol produced by the process. Drawn off from the column (32) via the line (38) is a residue which contains a mixture of water, hydrogen chloride, dichloropropanol and also other constituents of the reaction medium. This mixture may be completely or partly recycled to the reactor (26) via the line (39). The non-recycled part constitutes a purge. The weight ratio of the hydrogen chloride relative to the water in the flow drawn off from the line (39) is that of the water/hydrogen chloride azeotrope at a pressure of 0.1 bar, i.e. 0.3.

Figure 4:
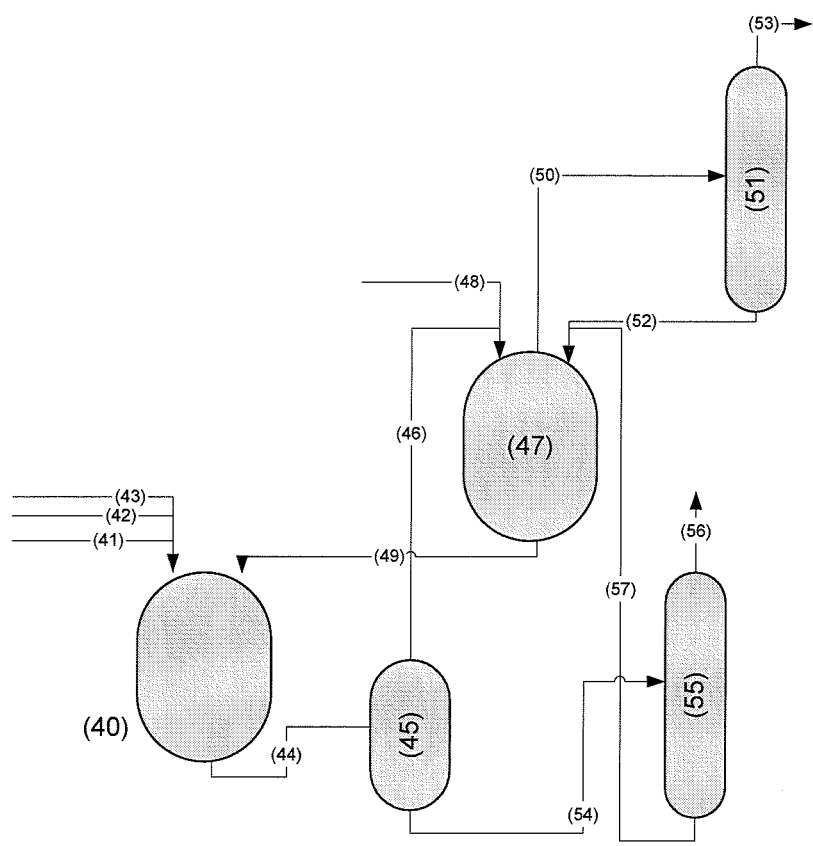

In a sixth combination of embodiments of the process according to the invention which is presented in FIG. 4, a first reactor (40) is continuously supplied with glycerol, gaseous hydrogen chloride and a catalyst respectively via the lines (41), (42) and (43). The reactor is permanently kept under a partial pressure of hydrogen chloride above the partial pressure of hydrogen chloride in the water/hydrogen chloride azeotrope at the reaction pressure. The reaction pressure is higher than or equal to 2 bar absolute.

A flow is drawn off from the reactor (40), continuously or in batch mode, via the line (44) in order to supply a flash evaporator (45), in which almost all of the hydrogen chloride and water contained in the flow (44) is vaporized. A gas flow is drawn off from the flash evaporator (45) via the line (46), in which the weight ratio of hydrogen chloride relative to water is greater than that of the azeotropic water/hydrogen chloride composition, and a reactor (47) is supplied with this flow. The reactor (47) is also supplied with a flow containing glycerol via the line (48) and with a flow drawn off from the column (55) via the line (57). A gas or liquid flow is drawn off from the reactor via the line (50) and the distillation column (51) is supplied with this flow. The weight ratio of hydrogen chloride relative to water is less than that of the azeotropic water/hydrogen chloride composition at the pressure of the column (51). A flow is drawn off, from the column (51) via the line (53), which contains water and dichloropropanol with a hydrogen chloride content of less than 1 g/l. A flow is drawn off, from the column (51) via the line (52), which contains, amongst other things, hydrogen chloride, water and dichloropropanol, and the reactor (47) is supplied with this flow. Another liquid flow is drawn off from the reactor (47) via the line (49) and the reactor (40) is supplied with this flow. Drawn off from the bottom of the flash evaporator (45), and via the line (54), is a flow which is practically free from hydrogen chloride, and the distillation column (55) is supplied with this flow. Drawn off from the top of the column (55), via the line (56), is a flow composed of practically pure dichloropropanol. Drawn off from the bottom of the column (55), via the line (57), is a flow comprising heavy compounds that mostly contain glycerol monochlorohydrin, catalyst, unconverted glycerol and chlorinated ethers, and the reactor (47) is supplied with this flow. A part of this flow (57) may be drawn off to supply a purge.

Figure 5:
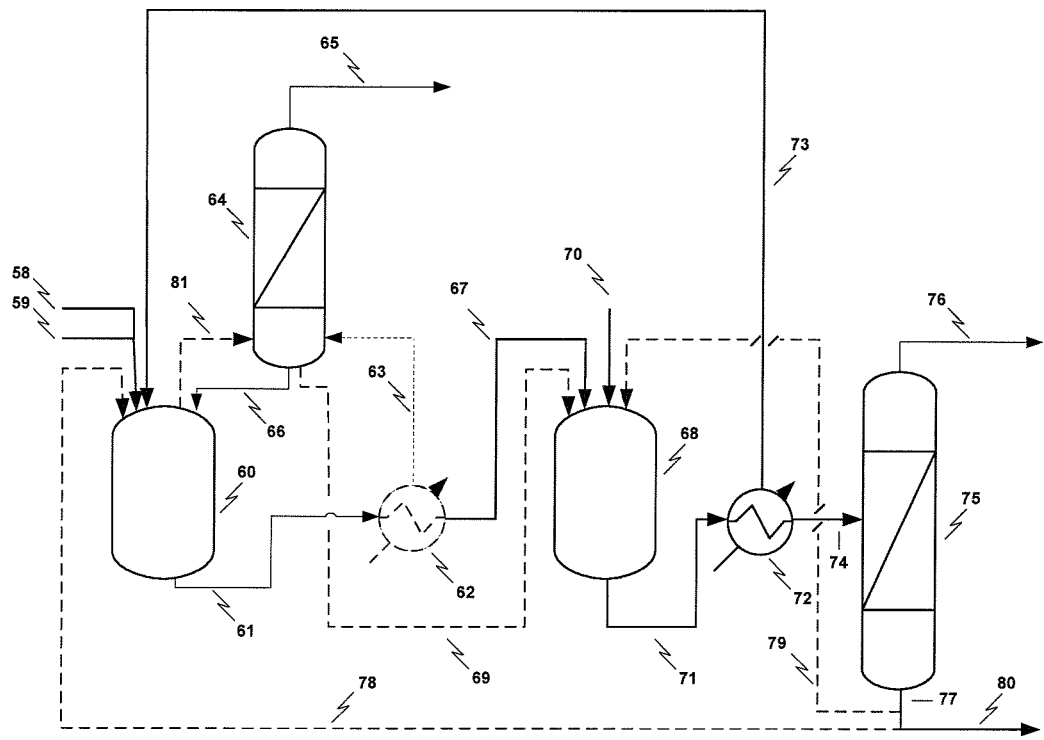

In a seventh combination of embodiments of the process according to the invention which is presented in FIG. 5, a second reactor (60) is continuously supplied with a flow containing glycerol and a flow containing a catalyst respectively via the lines (58) and (59). The reactor is also supplied with a mixture essentially composed of hydrogen chloride, water and dichloropropanol via a recycling flow (73) and with a mixture composed of glycerol, chloropropanediol, carboxylic acid and esters via a recycling flow (78). The reactor operates at close to atmospheric pressure. At least part of the gaseous phase from the reactor (60) is drawn off to supply the distillation column (64). A flow is drawn off continuously from the reactor (60) via the line (61) and an evaporator (62) is supplied with this flow. In the evaporator (62), almost all of the hydrogen chloride and water contained in the flow (61) is vaporized. A gas flow is drawn off from the evaporator (62) via the line (63) and a distillation column (64) is supplied with this flow. The weight ratio of hydrogen chloride relative to water in the flow (63) is less than that of the azeotropic water/hydrogen chloride composition at the pressure of the distillation column (64). A flow is drawn off, from the column (64) via the line (65), which contains water and dichloropropanol with a hydrogen chloride content of less than 1 g/l. A first flow is drawn off, from the base of the column (64) via the line (66) and the reactor (60) is supplied with this flow. A second flow is drawn off from the column (64) via the line (69) and a first reactor (68) is supplied with this flow so as to adjust the water content in the reaction mixture of the reactor (68). A liquid flow is drawn off from the evaporator (62) via the line (67) and the reactor (68) is supplied with this flow.

The reactor (68) is also supplied with a flow containing gaseous hydrogen chloride via the line (70). The reactor (68) is permanently kept under a partial pressure of hydrogen chloride above the partial pressure of hydrogen chloride in the water/hydrogen chloride azeotrope at the reaction temperature in the reactor (68). A liquid flow is drawn off from the reactor (68) via the line (71) and an evaporator (72) is supplied with this flow. Drawn off from the evaporator (72), via the line (73), is a gas flow essentially composed of hydrogen chloride, water and a little dichloropropanol, and the reactor (60) is supplied with this flow. Drawn off from the evaporator (72) via the line (74) is a liquid flow which is practically free from hydrogen chloride. This flow (74) supplies the column (75). Drawn off from the top of the column (75), via the line (76), is a flow containing practically pure dichloropropanol. Drawn off from the bottom of the column (75), via the line (77), is a flow which contains the heavy compounds from the reaction medium. These heavy compounds mostly contain glycerol monochlorohydrin, catalyst, unconverted glycerol and chlorinated ethers. A large part of this flow is recycled to the reactor (60) via the line (78). Another part of the flow drawn off from the bottom of the column (75) via the line (77) is conveyed to the reactor (68) via the line (79) so as to complete the conversion of chloropropanediol to dichloropropanol. Part of the flow drawn off from the bottom of the column (75) via the line (77) may supply a purge via the line (80).

In an eighth combination of embodiments of the process according to the invention, the same procedure as in the seventh combination of embodiments is followed, except that the liquid flow drawn off from the bottom of the column (64) is not conveyed to the reactor (68) via the line (69).

In a ninth combination of embodiments of the process according to the invention, the same procedure as in the seventh combination of embodiments is followed, except that the liquid flow drawn off from the bottom of the column (75) is not conveyed to the reactor (68) via the line (79).

In a tenth combination of embodiments of the process according to the invention, the same procedure as in the seventh combination of embodiments is followed, except that the liquid flow collected at the bottom of the column (64) is not conveyed to the reactor (68) via the line (69), and except that the liquid flow collected at the bottom of the column (75) is not conveyed to the reactor (68) via the line (79).

In an eleventh combination of embodiments of the process according to the invention, the same procedure as in the eighth combination of embodiments is followed, except that a gaseous phase is not drawn off from the reactor (60).

In a twelfth combination of embodiments of the process according to the invention, the same procedure as in the ninth combination of embodiments is followed, except that a gaseous phase is not drawn off from the reactor (60).

In a thirteenth combination of embodiments of the process according to the invention, the same procedure as in the tenth combination of embodiments is followed, except that a gaseous phase is not drawn off from the reactor (60).

The numbers cited between brackets in the remainder of the description refer to FIG. 5.

The invention also relates to a process for manufacturing dichloropropanol according to which glycerol and/or monochloropropanediol are reacted with hydrogen chloride, in a liquid reaction medium, which is in contact with a gaseous phase, in at least two reactors arranged in a loop, and under a partial pressure of hydrogen chloride in the first reactor (68) which is greater than the partial pressure of hydrogen chloride in the second reactor (60).

In one preferred operating mode, this process comprises, in addition, at least two separation operations, including one in at least one evaporator (72) in which the value of the partial pressure of hydrogen chloride is between the partial pressure of hydrogen chloride in the second reactor (60) and the partial pressure of hydrogen chloride in the first reactor (68) and including another in at least one distillation column (75), and in this process:

- the first reactor (68) is supplied with a first gas flow (70) containing hydrogen chloride and the second reactor with a first liquid flow (58) containing glycerol, and optionally water and hydrogen chloride, and a second liquid flow (59) containing a catalyst;
- drawn off from the first reactor (68) is a third liquid flow (71) and the evaporator (72) is supplied with this third liquid flow;
- drawn off from the evaporator (72) is a second gas flow (73) in which the weight ratio of hydrogen chloride with respect to water is greater than that of the azeotropic water/hydrogen chloride composition at total pressure in the evaporator (72) and the second reactor (60) is supplied with this second gas flow, drawn off from the evaporator (72) is a fourth liquid flow (74) of which the hydrogen chloride content is less than the hydrogen chloride content in the liquid reaction medium of the first reactor (68), and the first distillation column (75) is supplied with this fourth liquid flow (74);
- drawn off from the second reactor (60) is a fifth liquid flow (61=67) which supplies the first reactor (68), the evaporator (62) is not present and the lines (61) and (67) form a single line;
- drawn off from the first distillation column (75) is a third gas flow (76) which mostly contains dichloropropanol and a sixth liquid flow (77) which mostly contains reaction intermediates such as monochloropropanediol, the catalyst and reaction by-products such as partially chlorinated glycerol oligomers, and drawn off from the sixth liquid flow (77) is a seventh liquid flow (80) which constitutes a purge.

In a first variant of this preferred operating mode, the process comprises at least one additional separation step in a second distillation column (64) which is supplied with a fourth gas flow (81) drawn off from the second reactor (60), and drawn off from which second column is a fifth gas flow (65) which mostly contains water and dichloropropanol and an eighth liquid flow (66) which supplies the second reactor (60).

In a second variant of this preferred operating mode, the process comprises two additional separation steps, including one in a second evaporator (62) and including another in a second distillation column (64). The second evaporator (62) is supplied with the fifth liquid flow (61) and drawn off from the second evaporator (62) is a sixth gas flow (63) and a ninth liquid flow (67). The first reactor (68) is supplied with the ninth liquid flow (67). The second distillation column (64) is supplied with the sixth gas flow (63) and drawn off from the second distillation column (64) is an eighth liquid flow (66) which supplies the reactor (60).

In a third variant of this preferred operating mode, the procedure from the second variant is followed and in addition the second distillation column (64) is supplied with a gas flow (81) drawn off from the second reactor (60).

In supplementary variants, the procedure from the second or third variants is followed and, in addition, drawn off from the sixth liquid flow (77) is a tenth liquid flow (78) and the second reactor (60) is supplied with this flow, and/or drawn off from the sixth liquid flow (77) is an eleventh liquid flow

(79) and the first reactor (68) is supplied with this flow, and/or drawn off from the second distillation column (64) is a twelfth liquid flow (69) and the first reactor (68) is supplied with this flow.

The invention also relates to an installation for manufacturing dichloropropanol comprising at least two glycerol chlorination reactors arranged in a loop, at least one first reactor supply line (70), at least one second reactor supply line (58,59), and at least one line connecting the first and second reactor (61=67).

This installation preferably comprises, in addition, at least one evaporator (72) and at least one distillation column (75), at least one line (71) connecting the first reactor (68) and the evaporator (72), at least one line (74) connecting the bottom of the evaporator (72) and the first column (75), at least one line (73) connecting the top of the evaporator (72) and the second reactor (60), at least one outlet line (76) at the top of the first distillation column (75) and at least one outlet line (77) at the bottom of the first distillation column.

This preferred installation may comprise, in addition, a second distillation column (64), and at least two lines (66) and (81) connecting the bottom of the second distillation column (64) to the second reactor (60).

This preferred installation may comprise, in addition, a second evaporator (62) and at least one line (61) connecting the second reactor (60) to the second evaporator (62), a line (67) connecting the bottom of the second evaporator to the first reactor (68), at least one line (63) connecting the top of the second evaporator to the second distillation column (64).

This preferred installation may moreover comprise, in addition, at least one line (69) connecting the bottom of the second distillation column (64) and the first reactor (68), and/or at least one line (79) connecting the bottom of the first distillation column (75) and the first reactor (68), and/or at least one line (78) connecting the bottom of the first distillation column (75) and the second reactor (60).

The invention claimed is:

1. A process for manufacturing dichloropropanol comprising:
   (a) in a liquid reaction medium containing water, which is in contact with a gaseous phase, glycerol is reacted with hydrogen chloride under a partial pressure of hydrogen chloride in the gaseous phase greater than 0.2 base absolute to form dichloropropanol; and
   (b) at least part of the liquid reaction medium and optionally part of the gaseous phase from step a) is (are) subjected to at least one separation operation and, prior to said separation operation, the part of the liquid reaction medium and the part of the gaseous phase from step a) are subjected to:
   i. at least one treatment for reducing the weight ratio between the hydrogen chloride and the water in the part of the liquid reaction medium so as to attain a ratio less than or equal to the weight ratio between the hydrogen chloride and the water in a binary azeotropic hydrogen chloride/water composition at total pressure of the separation operation; and/or
   ii. at least one treatment for reducing the weight ratio between the water and the dichloropropanol in the part of the liquid reaction medium so as to attain a ratio less than or equal to the weight ratio between the water and the dichloropropanol in a ternary water/dichloropropanol/hydrogen chloride azeotrope at total pressure of the separation operation.

2. The process according to claim 1, wherein the treatment from step bi) comprises an operation chosen from the operations of evaporation, distillation and stripping of the part of the liquid reaction medium from step a), and combinations of at least two of them.

3. The process according to claim 1, wherein, at the end of the treatment from step bi), a first fraction comprising at least 80 wt % of hydrogen chloride and a second fraction comprising dichloropropanol that contains at most 30 wt % of hydrogen chloride are recovered.

4. The process according to claim 1, wherein the treatment from step bi) comprises an operation chosen from the operations of addition of glycerol and/or glycerol esters, of monochloropropanediol and/or monochloropropanediol esters and/or of a basic agent to the part of the liquid reaction medium from step a).

5. The process according to claim 1, wherein the treatment from step bi) comprises an operation chosen from the operations of addition of:
   (A) water; or
   (B) a dichloropropanol/water/hydrogen chloride mixture in which:
      1. the hydrogen chloride/water weight ratio is less than the weight ratio between the hydrogen chloride and the water in the binary azeotropic hydrogen chloride/water composition at total pressure of the separation operation; and/or
      2. the dichloropropanol/water weight ratio is less than the weight ratio between the water and the dichloropropanol in the ternary water/dichloropropanol/hydrogen chloride azeotrope at total pressure of the separation operation; or
   (C) a compound that forms an azeotrope with hydrogen chloride and water, and of which the boiling point is below the boiling point of the ternary water/dichloropropanol/hydrogen chloride azeotrope at total pressure of the separation operation; or
   (D) a salt-out salt,
   to the part of the liquid reaction medium from step a).

6. The process according to claim 1, wherein the treatment from step bi) comprises an operation chosen from the operations of adsorption and/or liquid/liquid extraction.

7. The process according to claim 1, wherein the part of the reaction medium obtained at the end of the treatment from step bi) is subjected to at least one operation of separation by distillation, recovered at the end of which is a first portion (I) comprising dichloropropanol and water, said portion containing at most 20 g of hydrogen chloride per kg of portion; and
   a second portion (IIa) comprising hydrogen chloride, water and dichloropropanol, and a third portion (Ma) containing dichloropropanol; or
   a second portion (IIb) comprising hydrogen chloride, water and dichloropropanol, and a third portion (IIIb) comprising hydrogen chloride and water; or
   a second portion (IIc) comprising hydrogen chloride and water, and a third portion (Mc) containing water.

8. The process according to claim 1, wherein the treatment from step bii) comprises an operation chosen from the operations of adsorption and/or liquid/liquid extraction.

9. The process according to claim 8, wherein the adsorption operation is carried out using an adsorbent chosen from molecular sieves having a pore size between 0.3 and 1 nm., and wherein the extraction operation is carried out using a semi-permeable membrane.

10. The process according to claim 1, wherein the part of the liquid reaction medium at the end of the treatment from step bii) is subjected to an operation chosen from the operations of evaporation, distillation and stripping.

11. The process according to claim 1, wherein the reaction is carried out in the presence of a catalyst.

12. The process according to claim 11, wherein the reaction is carried out in the presence of adipic acid as the catalyst.

* * * * *

UNITED STATES PATENT AND TRADEMARK OFFICE
CERTIFICATE OF CORRECTION

PATENT NO. : 8,471,074 B2
APPLICATION NO. : 12/529778
DATED : June 25, 2013
INVENTOR(S) : Philippe Krafft et al.

It is certified that error appears in the above-identified patent and that said Letters Patent is hereby corrected as shown below:

In the Claims:

Column 19 line 41 "base" should read --bar--
Column 20 line 43 "(Ma)" should read --IIIa--
Column 20 line 49 "(Mc)" should read --IIIc--

Signed and Sealed this
Tenth Day of September, 2013

Teresa Stanek Rea
*Acting Director of the United States Patent and Trademark Office*